(12) United States Patent
Kuhlmeier et al.

(10) Patent No.: US 11,168,358 B2
(45) Date of Patent: Nov. 9, 2021

(54) CHEMICAL HEATING SYSTEM FOR DIAGNOSTIC DEVICES

(71) Applicant: FRAUNHOFER-GESELLSCHAFT ZUR FORDERUNG DER ANGEWANDTEN FORSCHUNG, Munich (DE)

(72) Inventors: Dirk Kuhlmeier, Leipzig (DE); Vicky Troger, Leipzig (DE); Anja Scherber, Leipzig (DE); Natalia Sandetskaya, Leipzig (DE)

(73) Assignee: FRAUNHOFER-GESELLSCHAFT ZUR FORDERUNG DER ANGEWANDTEN FORSCHUNG, Munich (DE)

( * ) Notice: Subject to any disclaimer, the term of this patent is extended or adjusted under 35 U.S.C. 154(b) by 394 days.

(21) Appl. No.: 16/340,002

(22) PCT Filed: Oct. 4, 2017

(86) PCT No.: PCT/EP2017/075182
§ 371 (c)(1),
(2) Date: Apr. 5, 2019

(87) PCT Pub. No.: WO2018/065454
PCT Pub. Date: Apr. 12, 2018

(65) Prior Publication Data
US 2020/0032329 A1 Jan. 30, 2020

(30) Foreign Application Priority Data
Oct. 7, 2016 (EP) .................................... 16192764

(51) Int. Cl.
*C09K 5/18* (2006.01)
*C12Q 1/6844* (2018.01)

(52) U.S. Cl.
CPC .............. *C12Q 1/6844* (2013.01); *C09K 5/18* (2013.01)

(58) Field of Classification Search
CPC ................................ C12Q 1/6844; C09K 5/18
See application file for complete search history.

(56) References Cited

U.S. PATENT DOCUMENTS

| 4,522,190 A | 6/1985 | Kuhn et al. |
| 5,046,479 A | 9/1991 | Usui |
| 2005/0129582 A1 | 6/2005 | Breidford et al. |
| 2009/0004732 A1 | 1/2009 | LaBarre et al. |

(Continued)

FOREIGN PATENT DOCUMENTS

| CN | 204824862 U | 12/2015 |
| WO | 01/03619 A1 | 1/2001 |
| WO | 2014/154736 A1 | 10/2014 |

OTHER PUBLICATIONS

Hatano, et al., "LAMP Using a Disposable Pocket Warmer for Anthrax Detection, a Highly Mobile and Reliable Method for Anti-Bioterrorism", Jpn. J. Infect. Dis., 63, 36-40, 2010.

(Continued)

*Primary Examiner* — Jennifer Wecker
*Assistant Examiner* — Kathryn Elizabeth Limbaugh
(74) *Attorney, Agent, or Firm* — Tarolli, Sundheim, Covell & Tummino LLP

(57) ABSTRACT

The present invention relates to a chemical heating system for molecular diagnostic tests, comprising an air-activatable chemical heating composition, and a water-activatable chemical heating composition.

11 Claims, 1 Drawing Sheet

(56) References Cited

U.S. PATENT DOCUMENTS

2011/0294112 A1 12/2011 Bearinger et al.
2014/0154736 A1 6/2014 Puleo et al.

OTHER PUBLICATIONS

Liu, et al., "A self-heating cartridge for molecular diagnostics", Lab Chip, 2011, 11, 2686-2692.
Extended Search Report for Application No. 16192764.5-1404, dated May 4, 2017.
Raleigh, et al., "Air-activated chemical warming devices: Effects of oxygen and pressure", UHM 2005, vol. 32, No. 6.
Kubota, et al., "Non-Instrumented Nucleic Acid Amplification (NINA) for Rapid Detection of Ralstonia solanacearum Race 3 Biovar 2", Biol Eng Trans. 2011 ; 4(2): 69-80.
Weigl, et al., "Non-instrumented nucleic acid amplification assay", vol. 1, Jan. 1, 2008.
Singleton, et al., "Instrument-free exothermic heating with phase change temperature control for paper microfluidic devices", Proc SPIE. Mar. 9, 2013; 8615.
Curtis, et al., "Isothermal Amplification Using a Chemical Heating Device for Point-of-Care Detection of HIV-1", Feb. 2012, vol. 7, Issue 2.
Labarre, et al., "A Simple, Inexpensive Device for Nucleic Acid Amplification without Electricity—Toward Instrument-Free Molecular Diagnostics in Low-Resource Settings", May 2011, vol. 6, Issue 5.
Labarre, et al., "Non-Instrumented Nucleic Acid Amplification (NINA): Instrument-Free Molecular Malaria Diagnostics for Low-Resource Settings", Aug. 31-Sep. 4, 2010.

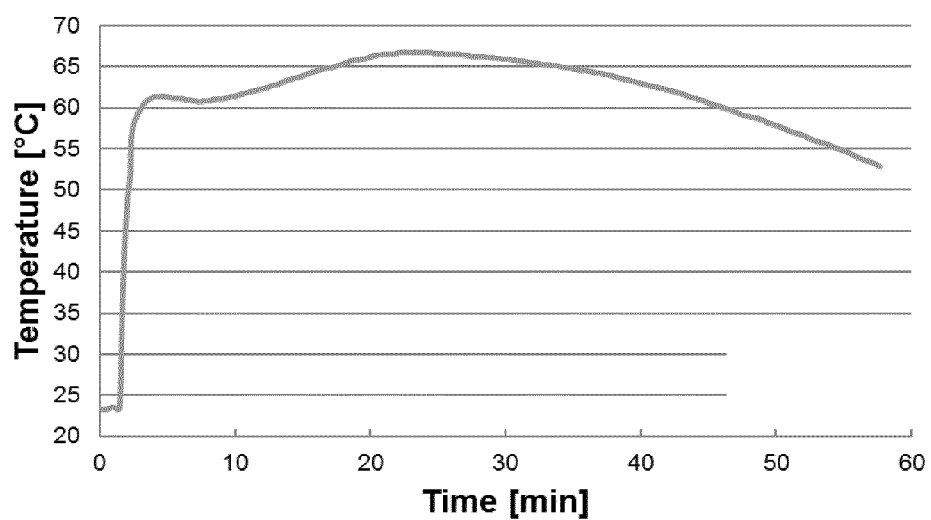

CHEMICAL HEATING SYSTEM FOR DIAGNOSTIC DEVICES

The present invention relates to a heating system for diagnostic devices.

Molecular diagnostic test methods are frequently including steps which need to be carried out at elevated but more or less constant temperature.

Diagnostic processes which require both heat and precise temperature control for proper device function are e.g. isothermal nucleic acid amplification, cell lysis, drying, incubation, and analytical reactions.

Meanwhile, a number of nucleic acid isothermal amplification processes are available. They need to be carried out within a narrow and well defined temperature range (typically varying by not more than +/−4° C.) for optimal enzyme performance. One of these amplification processes is loop-mediated isothermal amplification (LAMP). Other isothermal nucleic acid amplification processes are e.g. nucleic acid sequence-based amplification (NASBA), strand displacement amplification (SDA), rolling circle amplification (RCA), a Recombinase Polymerase Amplification (RPA), and helicase-dependent amplification (HAD).

While these isothermal conditions should be maintained throughout the entire amplification process (typically for a period of time ranging from minutes to an hour), it is also aimed at achieving said isothermal process temperature as quickly as possible. However, when heating up the molecular diagnostic platform too quickly, heat peaks might be generated, thereby exceeding the pre-defined temperature range.

Keeping a molecular diagnostic platform within a well-defined temperature range can be achieved by using electrical heating elements and electronic temperature control. However, there is meanwhile an increasing demand for point-of-care diagnostic devices which are easy to handle and provide precision temperature control without requiring electricity, high levels of infrastructure, or large and expensive equipment. Point-of-care testing is defined as diagnostic testing at or near the point of care, i.e. at the time and place of patient care.

For hand warmers and ready-to-eat meals, air-activatable or water-activatable chemical heating compositions are typically used. As known to the skilled person, air-activatable heaters or heating compositions are those which release heat by exothermic reaction between oxygen and a metal (in particular a transition metal such as iron). Optionally, such air-activatable chemical heating compositions may contain further additives which promote and/or catalyze the redox reaction between the metal and oxygen. As also known to the skilled person, water-activatable heaters or heating compositions are those which release heat by exothermic reaction between water and an appropriate reaction partner such as an alkaline earth metal oxide or an alkaline earth metal alloy.

U.S. Pat. No. 4,522,190 describes a heating pad which comprises a water-activatable chemical heating composition based on a magnesium alloy. Upon contact with water, an exothermic reaction according to reaction scheme (1) takes place, thereby activating the chemical heating composition.

$$Mg + 2H_2O \rightarrow Mg(OH)_2 + H_2 \qquad (1)$$

U.S. Pat. No. 5,046,479 describes a disposable body warmer which comprises an air-activatable chemical heating composition based on iron powder. Upon contact with air, an exothermic reaction between iron and oxygen takes place, thereby activating the chemical heating composition.

G. Raleigh et al., "Air-activated chemical warming devices: effects of oxygen and pressure", Undersea Hyperbar Med 2005 (32), pp. 445-449, study the effect of oxygen concentration on air-activated chemical heating compositions.

Electricity-free molecular diagnostic devices for isothermal biochemical processes (such as nucleic acid isothermal amplification) are known.

J. Singleton et al., Proc. SPIE, 2013 March 9; 8615: 86150R (doi:10.1117/12.2005928) describe a molecular diagnostic device having a non-electric heating system which comprises a phase change material (an eutectic mixture of myristic acid and stearic acid) and a water-activatable chemical heating composition (a magnesium alloy to be reacted with water). As illustrated in FIG. 4, the phase-change material is needed to absorb thermal energy of heat peaks after the heating-up period, thereby keeping the temperature within the pre-defined range.

This approach (i.e. combining a chemical heating composition with a phase change material) has been used by others as well, see e.g.

B. Hatano et al., "LAMP using a disposable pocket warmer for anthrax detection, a highly mobile and reliable method for anti-bioterrorism" Jpn. J. Infect. Dis., 63(1), 36-40 (2010);

C. Liu et al., "A self-heating cartridge for molecular diagnostics", Lab on a Chip, 11, 2686 (2011)

P. LaBarre et al., "Noninstrumented nucleic acid amplification (NINA): instrument-free molecular malaria diagnostics for low-resource settings", Conf. Proc. IEEE Eng. Med. Biol. Soc. (2010);

R. Kubota et al., "Noninstrumented nucleic acid amplification (NINA) for rapid detection of Ralstonia solanacearum race 3 biovar 2", Biol. Eng. Trans., 4(2), 69-80 (2011);

K. Curtis et al., "Isothermal amplification using a chemical heating device for point-of-care detection of HIV-1", PLoS One, 7(2), e31432 (2012);

P. LaBarre et al., "A simple, inexpensive device for nucleic acid amplification without electricity—toward instrument-free molecular diagnostics in low-resource settings", PLoS One, 6(5), e19738 (2011).

Heating systems containing a phase-change material need quite long warm-up phases until the pre-defined process temperature is achieved, and typically occupy quite a large volume.

An object of the present invention is to provide a heating system which heats up very quickly to a pre-defined process temperature and can maintain said process temperature within a narrow range for a time period which is sufficient for molecular diagnostic purposes (such as nucleic acid isothermal amplification). The heating system should be applicable in (portable and disposable) point-of-care molecular diagnostic devices.

The object is solved by a device which comprises
a diagnostic platform, and
a chemical heating system comprising
an air-activatable chemical heating composition, and
a water-activatable chemical heating composition.

As known to the skilled person, air-activatable heaters or heating compositions are those which release heat by exothermic reaction between oxygen and a metal (in particular a transition metal such as iron). Optionally, such air-activatable chemical heating compositions may contain further additives which promote and/or catalyze the redox reaction between the metal and oxygen.

As also known to the skilled person, water-activatable heaters or heating compositions are those which release heat by exothermic reaction between water and an appropriate reaction partner such as an alkaline earth metal oxide or an alkaline earth metal alloy.

In the present invention, it has surprisingly been realized that a combination of air-activatable and water-activatable chemical heating compositions allows for heating up very quickly to the desired process temperature of typical isothermal diagnostic test methods (e.g. molecular diagnostic tests, enzymatic tests, or immunological tests) and keeping said temperature sufficiently constant until the process is finished. Surprisingly, although the chemical heating system of the present invention shows a very high heating rate upon activation, no heat peak exceeding typical process temperatures of molecular diagnostic test methods is generated. Accordingly, no phase change material for absorbing excess reaction heat is needed.

Preferably, the water-activatable chemical heating composition comprises at least one of the following components: an alkaline earth metal oxide, an alkaline earth metal alloy, an alkali metal oxide, an alkali metal alloy, or a combination of at least two of these components.

A preferred alkaline earth metal oxide is calcium oxide, magnesium oxide, or a mixture thereof. A preferred alkali metal oxide is lithium oxide.

A preferred alkaline earth metal alloy is a magnesium-based alloy comprising at least one alloying element which is selected from Fe, Co, Cu, Ni, Zn, or Al or a combination of at least two of these alloying elements. Appropriate magnesium-based alloys for water-activatable chemical heating compositions are known to the skilled person. Typically, the magnesium-based alloy comprises the one or more alloying elements (preferably Fe) in a total amount of from 1 to 25 at %, more preferably from 2 to 20 at %, even more preferably 3 to 15 at %. Such alloys are commercially available (e.g. MgFe Fuel from Luxfer Magtech) or can be obtained by commonly known preparation methods. In a preferred embodiment, the alkaline earth metal alloy is a magnesium-based alloy containing Fe as an alloying element in an amount as specified above, the remainder being magnesium and unavoidable impurities.

Preferably, if the water-activatable chemical heating composition comprises an alkaline earth metal alloy (such as a magnesium-based alloy containing iron as an alloying element), it also comprises an inorganic salt, e.g. an inorganic halide salt such as NaCl. The weight ratio between the alkaline earth metal alloy and the inorganic salt can be e.g. from 5/1 to 1/2, or from 5/1 to 1/1.

If the water-activatable chemical heating composition comprises an alkaline earth metal oxide (such as CaO) or an alkali metal oxide (such as lithium oxide), no additional additive needs to be present in the water-activatable chemical heating composition. In other words, when using an alkaline earth metal oxide or alkali metal oxide, the water-activatable chemical heating composition can be a single-component composition.

Typically, the water-activatable chemical heating composition is provided in the form of a powder.

As indicated above, the chemical heating system of the present invention further comprises an air-activatable chemical heating composition.

Preferably, the air-activatable chemical heating composition comprises a transition metal powder. In a preferred embodiment, the transition metal is iron, or zinc, or a mixture thereof. The transition metal can be in its elementary form or can be an alloy.

For promoting the exothermic reaction between the transition metal and oxygen, it is preferred that the air-activatable chemical heating composition further comprises one or more solid additives which are selected from carbon, an inorganic salt, a silicate mineral, and a combination of at least two of these solid additives.

Exemplary types of carbon are e.g. activated carbon and charcoal. Typically, the solid carbon is provided in the form of a powder. The inorganic salt can be an inorganic halide salt (e.g. NaCl, KCl). The silicate mineral can be a phyllosilicate mineral, such as Vermiculite.

In a preferred embodiment, the air-activatable chemical heating composition comprises the transition metal powder (e.g. iron powder) in an amount of from 45 wt % to 75 wt %, more preferably from 55 wt % to 65 wt %, the carbon in an amount of from 10 wt % to 40 wt %, more preferably from 20 wt % to 35 wt %, the inorganic salt in an amount of from 5 wt % to 20 wt %, more preferably from 10 wt % to 15 wt %.

The exothermic reaction between the transition metal powder (e.g. iron powder) and oxygen can be further promoted in the presence of water. In principle, the air-activatable chemical heating composition may already contain water before its activation. If so, an aqueous medium containing the transition metal powder and optionally one or more of the solid additives mentioned above (e.g. carbon and an inorganic salt) can be surrounded by an oxygen-impermeable membrane, and by at least partially removing said membrane, the aqueous medium containing the transition metal powder comes into contact with atmospheric oxygen, thereby activating the chemical heating composition.

However, in a preferred embodiment, the air-activatable heating composition containing the transition metal powder and optionally one or more of the solid additives mentioned above can be provided in the form of a dry powder, and water for promoting oxidation of the transition metal is added at a later stage (e.g. when activating the heating composition by air). As will be described below in further detail, both the air-activatable chemical heating composition and the water-activatable chemical heating composition are preferably provided in the form of a powder, and water is added at a later stage in an amount which is sufficient for activating the water-activatable heating composition and promoting oxidation of the transition metal powder in the air-activatable composition.

Appropriate amounts of water for activating the water-activatable heating composition and promoting oxidation of the transition metal powder in the air-activatable composition can easily be adjusted by the skilled person. Typically, the weight ratio between the amount of water and the total amounts of the air-activatable and water-activatable heating compositions is within the range of from 1/1 to 1/4, more preferably from 1/2 to 1/3.

If an alkaline earth metal oxide (such as calcium oxide) or alkali metal oxide is present, the weight ratio between the transition metal powder (e.g. iron powder) and the alkaline earth metal oxide or alkali metal oxide is preferably from 6/1 to 1/2, more preferably from 5/1 to 1/1.

If an alkaline earth metal alloy (e.g. a magnesium-based alloy) or alkali metal alloy is present, the weight ratio between the transition metal powder (e.g. iron powder) and the alkaline earth metal alloy or alkali metal alloy is preferably from 50/1 to 3/1, more preferably from 35/1 to 4/1.

If the water-activatable chemical heating composition comprises the alkaline earth metal oxide or alkali metal oxide, it is preferred that the air-activatable chemical heating composition and the water-activatable chemical heating composition are not in direct contact with each other.

If the water-activatable chemical heating composition comprises the alkaline earth metal alloy or alkali metal alloy, the air-activatable chemical heating composition and the water-activatable chemical heating composition can be in direct contact with each other, e.g. in the form of a powder blend.

In an exemplary embodiment, the air-activatable chemical heating composition comprises iron powder, activated carbon, and an inorganic chloride salt such as NaCl, and is preferably provided as a dry blend; the water-activatable chemical heating composition comprises calcium oxide, preferably as a dry powder; wherein the air-activatable heating composition and the water-activatable heating composition are preferably not in direct contact with each other.

According to another exemplary embodiment, the air-activatable chemical heating composition comprises iron powder, activated carbon, and an inorganic chloride salt such as NaCl; the water-activatable chemical heating composition comprises a magnesium-based alloy containing iron as an alloying element; wherein the air-activatable heating composition and the water-activatable heating composition are preferably mixed with each other so as to provide a dry blend.

Preferably, the device or chemical heating system does not contain a phase change material (such as a paraffin, a fatty acid, a salt hydrate, or an eutectic mixture), in particular no phase change material showing a reversible phase transition (in particular a solid-liquid or solid-solid phase transition) at a temperature which lies within the temperature range at which the diagnostic test is carried out. Accordingly, in a preferred embodiment, the device or chemical heating system does not contain a phase change material showing a reversible phase transition within the temperature range of from 32° C. to 69° C., more preferably from 35° C. to 69° C. or from 40° C. to 69° C.

As already mentioned above, a combination of air-activatable and water-activatable chemical heaters allows for heating up very quickly to the desired process temperature of the molecular diagnostic test and keeping said temperature sufficiently constant until the process is finished. No electrical heating elements and no electronic temperature control means are needed. Accordingly, it is preferred that the device is free of any electrical heating elements and electronic temperature control means.

As the device can be of small size and does not include any harmful components, it is disposable and easily portable. Preferably, the diagnostic device is a point-of-care diagnostic device.

Of course, for heating up the molecular diagnostic platform, the chemical heating system and the molecular diagnostic platform are in thermal contact with each other. Appropriate configurations which allow efficient heat transfer from the chemical heating system to the molecular diagnostic platform are known to the skilled person. In an exemplary embodiment, the chemical heating system is present in a casing (e.g. a plastic casing or glass casing), and the molecular diagnostic platform is attached or fixed to said casing (e.g. to an outer or inner wall of said casing).

The casing has one or more inlets by which air and optionally water can enter into the casing. Just as an example, the inlet can be a hole or drilling in the casing wall, said hole or drilling being covered by an air-permeable membrane. Optionally, the membrane can be air- and water-permeable.

As the device is typically stored for a while before being activated and used in a diagnostic test, it can be vacuum-packed. Right before the diagnostic testing, the vacuum package is removed so that air can enter the casing which contains the air-activatable and water-activatable heating compositions. Then, water can be added for activating the water-activatable composition and optionally promoting the oxidation of the metal powder in the air-activatable composition.

In principle, it is also possible that water is already present in the casing before activation but is not in contact with the water-activatable heating composition. The water might be positioned in a (flexible or rigid) container separated from the water-activatable composition, and activation is achieved by releasing the water from said container so as to come into contact with the water-activatable composition, and optionally with the air-activatable composition.

As indicated above, the device further comprises a diagnostic platform.

Appropriate diagnostic platforms (i.e. platforms which are suitable for performing a diagnostic test) are known to the skilled person and might be e.g. a paper-based platform or a plastic-based platform. The diagnostic platform may comprise a microfluidic chip.

Preferably, the diagnostic platform is suitable for performing a molecular diagnostic test (also referred to as a molecular diagnostic platform or platform for molecular diagnostic testing). In a preferred embodiment, the molecular diagnostic platform is a platform for cell lysis and/or isothermal amplification of nucleic acids, such as a loop-mediated isothermal amplification (LAMP), a nucleic acid sequence-based amplification (NASBA), a strand displacement amplification (SDA), a rolling circle amplification (RCA), a Recombinase Polymerase Amplification (RPA), or a helicase-dependent amplification (HDA).

Isothermal process condition can be relevant for enzymatic and/or immunological tests as well. Accordingly, the diagnostic device of the present invention may comprise a diagnostic platform which is suitable for performing an enzymatic test (also referred to as an "enzymatic diagnostic platform" or "diagnostic platform for enzymatic testing") or an immunological test (also referred to as an "immunological diagnostic platform" or "diagnostic platform for immunological testing").

Furthermore, the present invention relates to a use of the chemical heating system or the device as described above for performing a diagnostic test.

With regard to the properties of the chemical heating system or the device, reference can be made to the statements provided above.

As already mentioned above, both the air-activatable chemical heating composition and the water-activatable chemical heating composition are preferably provided in the form of a powder, and water is added in an amount which is sufficient for activating the water-activatable heating composition and promoting oxidation of the transition metal powder in the air-activatable composition.

The diagnostic test can be a molecular diagnostic test. Preferably, the molecular diagnostic test comprises a cell lysis step and/or an isothermal amplification of nucleic acids, such as a loop-mediated isothermal amplification (LAMP), a nucleic acid sequence-based amplification (NASBA), a strand displacement amplification (SDA), a rolling circle amplification (RCA), a Recombinase Polymerase Amplification (RPA), or a helicase-dependent amplification (HDA).

In the present invention, it is also possible that the diagnostic test is an enzymatic test or an immunological test.

Preferably, the device or chemical heating system is used for a point-of-care diagnostic test.

Preferably, the diagnostic test is performed in a temperature range of from 32° C. to 69° C., more preferably from 35° C. to 69° C. or from 40° C. to 69° C., wherein the temperature varies by not more than +/−4° C. for at least 10 minutes, more preferably at least 20 minutes.

The invention is described in further detail by the following Examples:

EXAMPLE 1

A blend of iron powder (4.5 g), activated carbon (1.7 g) and sodium chloride (0.9 g), representing the air-activatable chemical heating composition, is provided in a plastic casing. Calcium oxide (2.0 g), representing the water-activatable chemical heating composition, is shrink-wrapped in a water-soluble foil which is then also provided in said plastic casing.

The casing topside contains several openings by which air and water can enter the casing.

A molecular diagnostic platform is fixed to the plastic casing.

The device is vacuum-packed so that no air can enter the casing which contains the chemical heating system. By removing the vacuum package, air enters the casing. Then, water (4 ml) is added for activating the water-activatable composition and promoting the oxidation of the metal powder in the air-activatable composition.

The water-soluble foil is at least partly dissolved and an exothermic reaction between CaO and water is initiated. Furthermore, the water is promoting the exothermic redox reaction between the metal powder and the atmospheric oxygen. The reaction heat is transferred to the molecular diagnostic platform fixed to the casing wall.

Temperature at the platform as a function of time is measured. The temperature curve is shown in FIG. 1.

As demonstrated by the measured curve, there is an extremely sharp increase of temperature to about 61° C. and said temperature is maintained within a relatively narrow range for more than 40 minutes. Under these temperature conditions, a loop-mediated isothermal amplification (LAMP) can be carried out. No phase change material is needed.

By varying the amounts of the water-activatable and air-activatable compositions, the temperature to which the diagnostic platform is heated up can be adjusted, depending on the type of isothermal diagnostic test to be carried out.

EXAMPLE 2

The air-activatable heating composition was a mixture of iron powder, activated carbon, and sodium chloride. The water-activatable composition was a magnesium-iron alloy (Fe content: 13 at %).

The air-activatable and water-activatable heating compositions were mixed, thereby obtaining a final blend containing iron powder (4.2 g), activated carbon (2.4 g), sodium chloride (0.9 g) and the magnesium-iron alloy (0.2 g).

The blend was positioned in the same plastic casing as used in Example 1. A molecular diagnostic platform is fixed to the plastic casing.

By removing the vacuum package, air enters the casing. Then, water was added (3 ml). An exothermic reaction between magnesium and water is initiated. Furthermore, the water is promoting the exothermic reaction between the iron powder and the atmospheric oxygen. The reaction heat is transferred to the molecular diagnostic platform fixed to the exterior of the casing.

Similar to Example 1, temperature at the molecular diagnostic platform was increasing to a value of about 65° C. within a short period of time and said temperature was maintained within a relatively narrow range for at least 15 minutes. Under these temperature conditions, a loop-mediated isothermal amplification (LAMP) can be carried out. No phase change material is needed.

By varying the amounts of the water-activatable and air-activatable compositions, the temperature to which the diagnostic platform is heated up can be adjusted, depending on the type of isothermal diagnostic test to be carried out.

The invention claimed is:

1. A device comprising: a diagnostic platform, and a chemical heating system comprising: both an air-activatable chemical heating composition which comprises a transition metal powder, and a water-activatable chemical heating composition which comprises a component which is selected from an alkaline earth metal oxide, an alkaline earth metal alloy, an alkali metal oxide, and an alkali metal alloy.

2. The device according to claim 1, wherein the alkaline earth metal oxide is calcium oxide, or magnesium oxide or a mixture thereof; or wherein the alkaline earth metal alloy is a magnesium-based alloy comprising at least one alloying element which is selected from Fe, Co, Cu, Ni, Zn, or Al or a combination of at least two of these alloying elements.

3. The device according to claim 1, wherein the transition metal is iron or zinc.

4. The device according to claim 1, wherein the air-activatable chemical heating composition further comprises one or more solid additives which are selected from the group consisting of carbon, an inorganic salt, a silicate mineral, and a combination of at least two of these solid additives.

5. The device according to claim 1, wherein the water-activatable chemical heating composition comprises an alkaline earth metal oxide, and the air-activatable chemical heating composition and the water-activatable chemical heating composition are not in direct contact with each other.

6. The device according to claim 1, wherein the water-activatable chemical heating composition comprises an alkaline earth metal alloy, and the air-activatable chemical heating composition and the water-activatable chemical heating composition are in direct contact with each other in the form of a powder blend.

7. The device according to claim 1, wherein no phase change material is present.

8. The device according to claim 1, wherein the diagnostic platform is a platform for molecular diagnostic testing, enzymatic testing, or immunological testing.

9. The device according to claim 1, being free of any electrical heating elements and electronic temperature control means.

10. The device according to claim 1, wherein the chemical heating system is positioned in a casing and the molecular diagnostic platform is fixed to the casing.

11. The device according to claim 10, wherein the casing has one or more inlets by which air and optionally water can enter the casing.

\* \* \* \* \*